(12) United States Patent
Rechberg (10) Patent No.: US 8,998,822 B2
(45) Date of Patent: Apr. 7, 2015

(54) PORTABLE PREPROGRAMMED THERMOMETER FOR INDICATING FERTILITY STATUS

(75) Inventor: Natalie Rechberg, Zurich (CH)

(73) Assignee: Valley Electronics LLC, Eden, MD (US)

( * ) Notice: Subject to any disclaimer, the term of this patent is extended or adjusted under 35 U.S.C. 154(b) by 384 days.

(21) Appl. No.: 13/418,385

(22) Filed: Mar. 13, 2012

(65) Prior Publication Data

US 2012/0238900 A1    Sep. 20, 2012

Related U.S. Application Data

(60) Provisional application No. 61/452,296, filed on Mar. 14, 2011.

(51) Int. Cl.
*A61B 5/00* (2006.01)
*A61B 10/00* (2006.01)

(52) U.S. Cl.
CPC .................. *A61B 10/0012* (2013.01)

(58) Field of Classification Search
CPC .......................... A61B 10/0012; A61B 17/425
USPC ..................... 600/551, 591; 702/19
See application file for complete search history.

(56) References Cited

U.S. PATENT DOCUMENTS

| | | |
|---|---|---|
| 3,749,089 A | 7/1973 | Derr |
| 3,924,609 A | 12/1975 | Friedenberg |
| 3,926,037 A | 12/1975 | Kopito |
| 3,928,423 A | 12/1975 | Samour |
| 3,986,494 A | 10/1976 | Preti |
| 4,002,056 A | 1/1977 | Kopito |
| 4,010,738 A | 3/1977 | Preti |

(Continued)

FOREIGN PATENT DOCUMENTS

| | | |
|---|---|---|
| JP | 2007-071776 | 3/2007 |
| JP | 2009-045155 | 3/2009 |

OTHER PUBLICATIONS

Valley Electronics LLC, 25505 Collins Wharf Rd, Eden, MD 21822, advertising brochure, and instructions for using the "Lady-Comp" fertility monitoring device. Those brochures are available as free downloads at http://www.lady-comp.com/en.

(Continued)

*Primary Examiner* — Max Hindenburg
(74) *Attorney, Agent, or Firm* — Pillsbury Winthrop Shaw Pittman LLP (57) ABSTRACT

A method of recording, storing, analyzing, and displaying changes in a woman's basal body temperature includes the steps of: (a) recording with an intelligent, preprogrammed thermometer the woman's orally-measured temperature; (b) storing in the thermometer the woman's temperature to create a stored temperature reading; (c) repeating steps (a) and (b); (d) analyzing inside the thermometer the significance of any changes in the stored temperature readings; and (e) displaying the changes in the woman's basal body temperature, and displaying an analysis of those changes, on the thermometer, and on any electronic device connected to the thermometer. In other features of the invention, steps (a) and (b) are repeated daily when the woman first awakes from her night's sleep, and the woman first inputs into the thermometer data about herself, including at least her year of birth, her height, her weight, her body mass index, and her current and past menstruation data.

19 Claims, 6 Drawing Sheets

(56) References Cited

U.S. PATENT DOCUMENTS

| | | |
|---|---|---|
| 4,013,066 A | 3/1977 | Schuster |
| 4,031,365 A | 6/1977 | Raggiotti |
| 4,036,212 A | 7/1977 | Karuhn |
| 4,059,986 A | 11/1977 | Schuster |
| 4,119,089 A | 10/1978 | Preti |
| 4,148,304 A | 4/1979 | Mull |
| 4,151,831 A | 5/1979 | Lester |
| 4,151,833 A | 5/1979 | Polishuk |
| 4,246,907 A | 1/1981 | Bullock |
| 4,465,077 A | 8/1984 | Schneider |
| 4,475,158 A | 10/1984 | Elias |
| 5,050,612 A | 9/1991 | Matsumura |
| 5,657,762 A | 8/1997 | Coley |
| 6,110,125 A * | 8/2000 | Young et al. ............ 600/551 |
| 6,419,637 B1 * | 7/2002 | Cheng et al. ............ 600/551 |
| 6,861,079 B2 | 3/2005 | Sweazy |
| 7,214,196 B2 | 5/2007 | Kodama et al. |
| 7,957,794 B2 * | 6/2011 | Hochman et al. ............ 600/546 |
| 8,374,989 B2 * | 2/2013 | Lee et al. ............ 706/52 |
| 8,679,013 B2 * | 3/2014 | Ziarno et al. ............ 600/301 |
| 2004/0081024 A1 | 4/2004 | Weng |
| 2004/0171964 A1 | 9/2004 | Heitz |
| 2006/0135885 A1 | 6/2006 | Iijima et al. |
| 2007/0191729 A1 | 8/2007 | Park |
| 2009/0054738 A1 | 2/2009 | Chou et al. |
| 2009/0326410 A1 * | 12/2009 | James et al. ............ 600/551 |
| 2013/0054150 A1 | 2/2013 | Sacks et al. |

OTHER PUBLICATIONS

Supplemental Search Report issued Jul. 11, 2014 in corresponding application No. EP12758308.

* cited by examiner

PORTABLE PREPROGRAMMED THERMOMETER FOR INDICATING FERTILITY STATUS

CROSS-REFERENCE TO RELATED APPLICATIONS

This patent application claims the benefit of provisional patent application Ser. No. 61/452,296, filed Mar. 14, 2011.

BACKGROUND OF THE INVENTION (1) Field of the Invention

The invention relates to methods and devices for measuring, analyzing, and displaying a woman's daily fertility status.

(2) Description of Related Art (Including Information Disclosed Under 37 CFR 1.97 and 1.98)

Measuring the "Basal Body Temperature" ("BBT") is a known method of fertility calculation. However, in the past a woman had to put the self-measured data on a graph each time that she took her temperature; the calculation and analysis were done manually by her. This is time consuming; human error can not be excluded. Other natural family planning devices exist. Existing devices such as fertility monitors and ovulation predictors use indications such as BBT, saliva, mucous analysis, or the measurement of hormonal changes in salvia or urine to depict ovulation.

Many monitoring methods have been patented, based on a wide variety of physical or chemical bodily changes believed to be indicative of the progress of the ovulation cycle. The following patents and patent applications are examples of such methods.

U.S. Pat. No. 3,749,089 describes an instrument for monitoring ovulation including a dual electrode vaginal probe and monitoring device, for indicating the magnitude and polarity of the electrochemical response of vaginal fluids.

U.S. Pat. No. 3,924,609 describes a test procedure and apparatus for determining low DC potentials for measurement and identification of the different phases as well as the fact of ovulation in adult mammalian females.

U.S. Pat. No. 3,926,037, U.S. Pat. No. 3,928,423, U.S. Pat. No. 4,002,056, U.S. Pat. No. 4,013,066 and U.S. Pat. No. 4,059,986, describe devices for determining the properties (particularly surface tension) of bodily mucus as an indication of menstrual cycle phase.

U.S. Pat. No. 3,986,494 and U.S. Pat. No. 4,010,738 describe a method of monitoring the concentration of volatile organic compounds having a molecular weight of between 50 and 350, found in vaginal secretions.

U.S. Pat. No. 4,031,365 describes a system for continuously monitoring and displaying temperature to indicate ovulation activity.

U.S. Pat. No. 4,036,212 describes a method of monitoring the progress of the ovulation cycle which comprises periodically determining the concentration of ATP in vaginal fluid.

U.S. Pat. No. 4,119,089 describes a method for predicting and ascertaining the time of ovulation by monitoring the level of at least one volatile sulphur compound commonly occurring in mouth air.

U.S. Pat. No. 4,148,304 describes a system for determining the time of ovulation in females including an ear probe which measures body temperature and a probe which measures body potential together with an electronic amplification circuit and indicating device which is capable of measuring small changes in temperature and body potential and providing a portable and, convenient device for determining time of ovulation.

U.S. Pat. No. 4,151,831 describes a fertility indicator for measuring and detecting the body temperature of a human subject over a menstrual cycle, having a timer for generating time based signals, and a logic circuit connected to the clock timer and being responsible to the time based signals for selecting the proper combinations of the time based signals and for indicating the correct present time. There are various types of temperature sensors (vaginal probe, mouth probe, or waist belt) that can be used, coupled to a logic circuit for measuring the body temperature of the human subject. A solid state memory circuit having coded information command signals is coupled to the logic circuit for sequencing the logic circuit to take a plurality of temperature readings at a preset real time and to terminate the readings when the temperature has stabilized. A data storage circuit is provided for sequentially recording each of the stabilized temperatures that were measured, and a display circuit responsive to the solid state memory and data storage circuits, indicates the status of fertility of the subject during a menstrual cycle. There is also an alarm circuit coupled to, the logic circuit and it has a variable pitch responsive to the solid state memory circuit for indicating the time when the subject's temperature has to be taken. Lights or words can indicate the user's status.

U.S. Pat. No. 4,151,833 describes a method for detecting ovulation by measuring the water content of the cervical mucus using a pellet made from a water-swellable polymer.

U.S. Pat. No. 4,246,907 describes a method for predicting ovulation based on measuring every day throughout at least a substantial portion of the days of the menstrual cycle, the polarity of a direct current potential between at least two spaced apart portions of a woman's body.

U.S. Pat. No. 4,465,077 describes a fertility computer having the ability to store information about a user's past menstrual cycle history, basal body temperature, and gynaecological disorders which; along with certain prediction indicators, is used to predict statistically when ovulation will occur. The information is processed in accordance with a pre-determined program which ascribes certain values to the parameters to predict the present fertility status of the user.

U.S. Pat. No. 5,657,762 describes a method of monitoring the ovulation cycle of a female mammal, involving regular measurement of basal body temperature throughout a current ovulation cycle and occasional measurement of the level of at least one urinary component of significance in the cycle, the measurement of the urinary component being conducted at predetermined stages in the cycle to check that the level is consistent with a predicted level and thus confirm that the cycle as a whole is consistent with a prediction.

U.S. Pat. No. 6,110,125 describes an indicating device for menstruation that includes: an ear-temperature measuring sensor to measure basal body temperatures of a user and output the measured values; a parameter-inputting means for inputting user-inputting parameters; a microprocessor for storing the basal body temperatures from the temperature measuring sensor, and storing the user-inputting parameters from the parameter inputting means, then using a mathematical method to estimate the user's monthly gynecophysiological factors in accordance, with the basal body temperatures and the user-inputting parameters; and a display means to display the user's monthly gynecophysiological factors estimated by the microprocessor. The indicating device for menstruation uses a mathematical method including weighting coefficients to estimate a user's monthly gynecophysiological factors more accurately.

U.S. Pat. No. 6,861,079 describes a basal body temperature thermometer and a chart with instructions to confirm when and if ovulation will/did occur. Commercially available urinary chemical reagent strips are provided with instructions so as to predict/confirm if and when ovulation will occur.

U.S. Pat. Application No. 20040081024 describes a wristwatch for taking the basal body temperature of a female and predicting her ovulation phase. The wristwatch has all of the following inside its case: a control circuit; a display; a memory; a timer; a battery; a wrist-temperature sensor, and a computer.

U.S. Pat. Application No. 20070191729 describes a basal body temperature ("BBT") measurement method which includes: measuring each distance to at least one ear canal area by emitting a pulse to a user's ear canal; measuring a body temperature in the ear canal area utilizing infrared rays; recognizing a first body temperature, corresponding to a first distance which satisfies a predetermined standard, as the user's eardrum temperature; and converting the eardrum temperature into the user's BBT.

A device that separates the thermometer from data entry, data analysis, data storage, and data display, is currently sold in the United States by Valley Electronics LLC, in Eden, Md., (web page is http://www.lady-comp.com/en/) as the "Lady-Comp" device, which connects a temperature probe via an extendible, flexible cord to a hand-held device that accepts the temperature measurement, compares it with past temperature measurements, analyzes all the data, determines fertility status, and then displays that status. However, the thermometer must stay connected via its cord to the hand-held device, while measuring the woman's temperature.

None of the systems described above uses a personal electronic device as a user interface in combination with an intelligent thermometer, which does all the calculations needed for the analysis of the female cycle, and which also displays the woman's fertility status. The only known existing systems using both a personal electronic device and an intelligent thermometer are of two types: first, a thermometer without cycle analysis combined with analysis application on the personal electronic device; and second, an intelligent preprogrammed thermometer with cycle analysis and readout capability. End user interaction (settings, editing menstruation recordings, etc.) is not intended to be done with the personal electronic device. The first type has the disadvantage that the temperature values have to be transferred manually to the personal electronic device, thus giving rise to possible mistakes, and is uncomfortable. The second type lacks the possibility to enter user information (Such as menstruation data) directly into the personal electronic device in a way that the consistency of data with the intelligent preprogrammed thermometer is assured.

In light of the foregoing, a need remains for a system and method to allow the appraisal of a woman's menstrual cycle (i.e. corpus luteum insufficiency, anovulation, ovulation) through the use of a small oral thermometer which can analyze, store, and display fertility status, and then also communicate with a woman's personal electronic device, or personal digital assistant, such as a Blackberry, an iPod or some other such "smart" phone to store and display the fertility status.

BRIEF SUMMARY OF THE INVENTION

An intelligent preprogrammed oral thermometer measures the basal body temperature to, track a woman's menstrual cycle to determine the fertile window. The thermometer is synced with a woman's personal electronic device using a software application to display the calculated fertility status.

It is an object of the present invention to provide a compact and portable product package, which includes an intelligent thermometer, sync software, and application software, to be used with a personal electronic device to analyze and display a woman's daily fertility status. A secondary object of the invention is to allow the appraisal of a woman's menstrual cycle (i.e. corpus luteum insufficiency, anovulation, ovulation) through the use of a small oral thermometer which communicates with a woman's personal electronic device.

BRIEF DESCRIPTION OF THE SEVERAL VIEWS OF THE DRAWINGS

The novel features characteristic of the invention are set forth in the appended claims. However, the invention itself, as well as a preferred mode of use, and further objectives and advantages thereof, will best be understood by reference to the following detailed description, when read, in conjunction with the accompanying drawings in which the left-most significant digit(s) in the reference numerals denote(s) the first figure in which the respective reference numerals appear.

DETAILED DESCRIPTION OF THE INVENTION

Figure 1A:
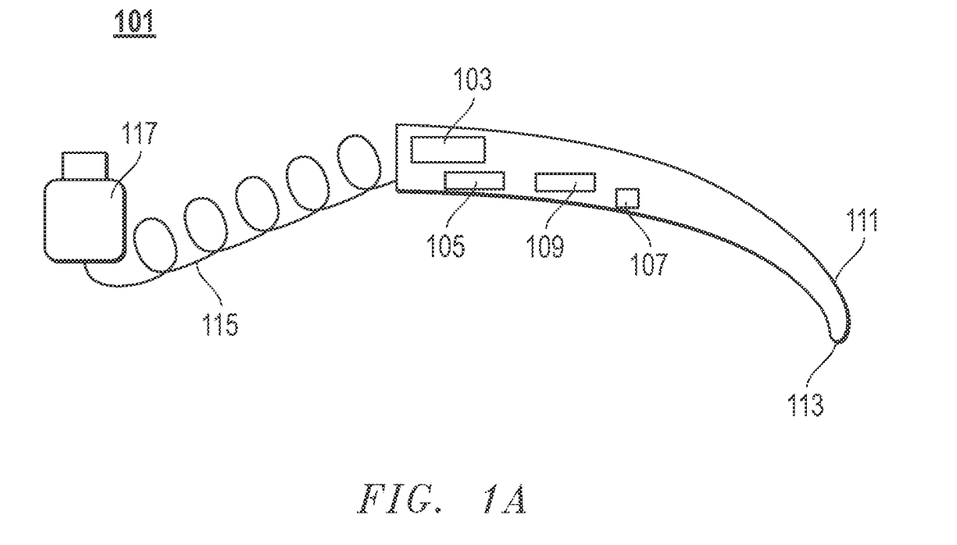
FIG. 1A is a schematic diagram of the intelligent preprogrammed thermometer of the present invention, equipped with a USB connection.

Referring now to FIG. 1A, a thermometer 101 is a portable, digital, intelligent, pre-programmed thermometer. The thermometer 101 measures a female's basal body temperature ("BBT"). The thermometer 101 contains a battery 105. An activation button 107 enables input of the first day of menstruation as it occurs in the user's female cycle, and allows the daily recordation of the BBT. The thermometer 101 includes a LED display 109 which indicates when measurement is successfully taken (about sixty seconds daily), and shows the actual daily fertile status of the user. In other embodiments, the display 109 can be replaced with, or accompanied by, either a light or an acoustic signal generator. The thermometer 101 has a resolution of ¹/₁₀₀ degrees Celsius. The thermometer 101 has a tip 111 which is designed to fit under a woman's tongue. The tip 111 includes a temperature sensor 113. A cable 115 attaches at a first end to the thermometer 101 and at a second end to a USB connector 117.

The thermometer 101 has a microcontroller chip 103. The microcontroller chip 103 contains the following items, hot shown in the drawings: a battery-backed volatile memory ("RAM"), a non-volatile memory (typically FLASH) for storing programs (plus an optional boot loader) and data ("ROM"), a CPU, an analog-to-digital converter ("ADC"), timers, a real-time clock with, an alarm function (with low power microcontrollers as MSP430 emulated by software), input lines for button(s) or optionally touch sense input pins, output lines for LED, sound, and/or displays (LCD, OLED or similar), and a voltage regulator. The microcontroller chip 103 is pre-programmed with temperature detection software, bio-mathematical forecasting software, synchronization recognition software, and application communication software.

Figure 1B:
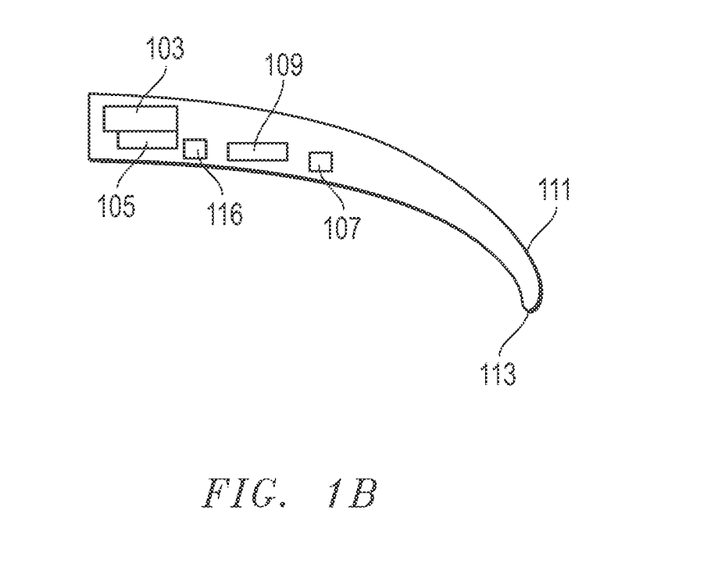
FIG. 1B is a schematic diagram of the intelligent preprogrammed thermometer of the present invention, equipped with a wireless connection.

Referring now to FIG. 1B, in an alternate embodiment of the thermometer 101, instead of using, the cable 115, the thermometer 101 is equipped with a wireless transducer chip 116 to enable wireless communication (for example, "Bluetooth").

The thermometer 101 can be used alone, or with a software application on the user's computer or other personal electronic device. The microcontroller chip 103 has enough storage capacity to store and display the female's fertile status. The necessary menstruation date can be input in three consecutive days by pressing the activation button 107 when menstruation occurs. The measurement of the BBT is taken daily, upon waking up, by putting the tip 111 under the tongue, and pressing the activation button 107. The temperature can only be taken once a day, within the temperature reading time limit. The temperature reading time limit comprises 6 hours, beginning and ending three hours before and after the last temperature reading time. Temperature can be taken only once a day within the time, limit for taking the temperature. If the user is within the reading time limit, she can take her temperature, as indicated by the notification alert 109. The alert 109 can be a light, a display, or an acoustic signal. The alert 109 indicates the end of measurement, and will show the fertile status of the actual day as either fertile, non fertile, or ovulation.

Figure 2:
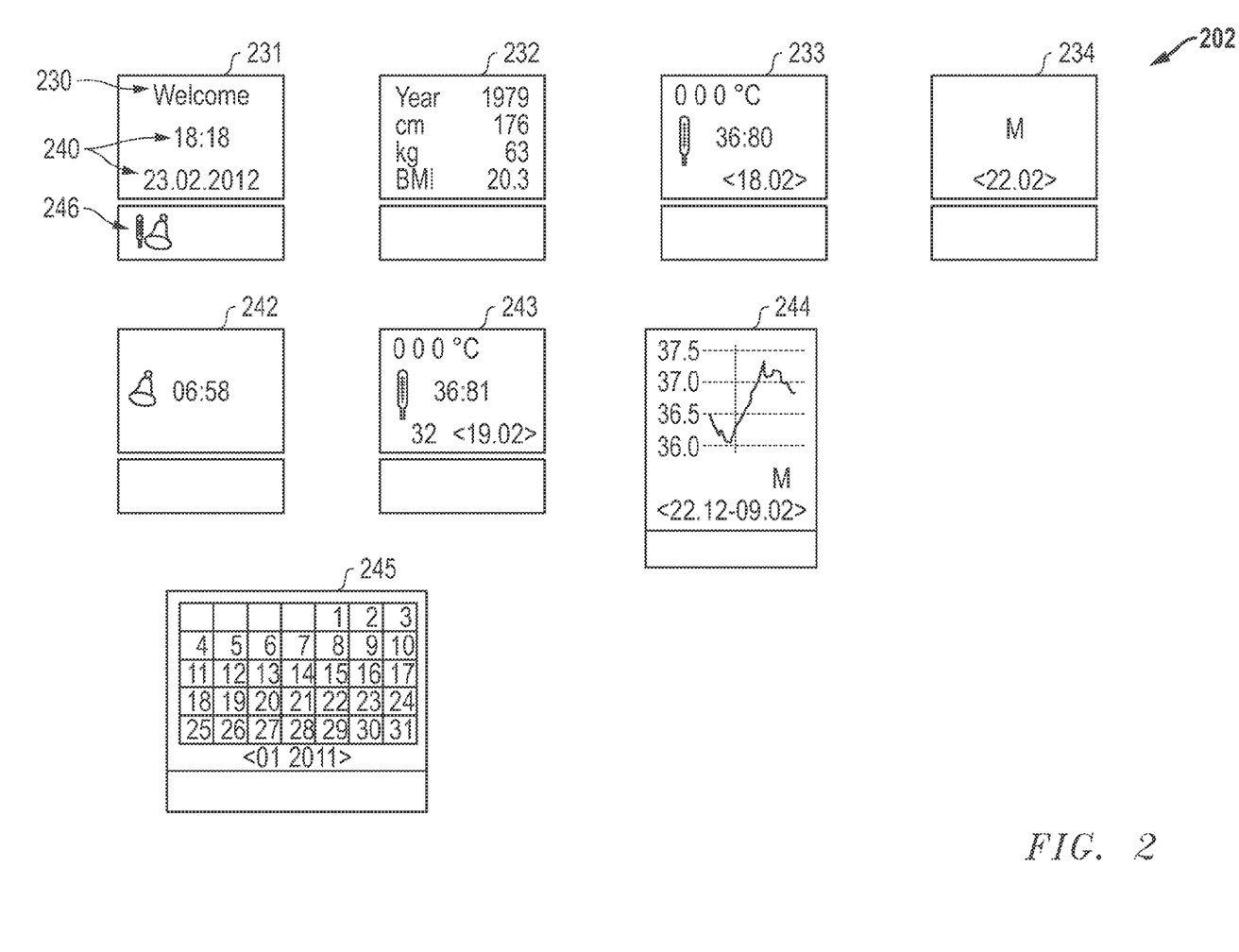
FIG. 2 illustrates various display screens on a woman's personal electronic device, when such device is loaded with the application software of the present invention.

Referring now to FIG. 2, application software 202 displays the results of the measurements taken, and the analysis done, by the thermometer 101. The application software 202 generates a main screen 231, which displays a welcome screen 230 and a footer navigation 240, which defaults to the current time and the date of the last fertility status. The format of the time and date can be changed to the user's local time and date by using the input language of the user's private electronic device 301, shown in FIG. 3. The footer navigation 240 contains the most used functions: a temperature reading, a fertility status, an alarm, and other settings. All functions of the footer navigation 240 are presented by an icon 246. After a tap on the welcome screen 230, a user data screen 232 allows the user to enter her year of birth, her height, her weight, and her body mass index ("BMI").

A display screen 233 presents the current temperature reading right after measurement. Using display screen 234, past or current menstruation data can be entered. (Occurring menstruation data is a necessary input used to calculate the users cycle.) Menstruation must be entered three consecutive days during each cycle. A display screen 242 allows the user to adjust and activate an alarm time. A display screen 243 presents the fertility status of the next 24 hours, calculated by the thermometer 101, and communicated to the application 202. The display screen 243 displays the menstrual cycle day, the measured temperature, the date, and other necessary indications. A display screen 244 shows the user's menstrual graph, depicting ovulation day, fertility status, phases of the moon, temperature reading, date, and forecast. A display screen 245 presents an overview of the woman's individual cycle calendar.

Figure 3:
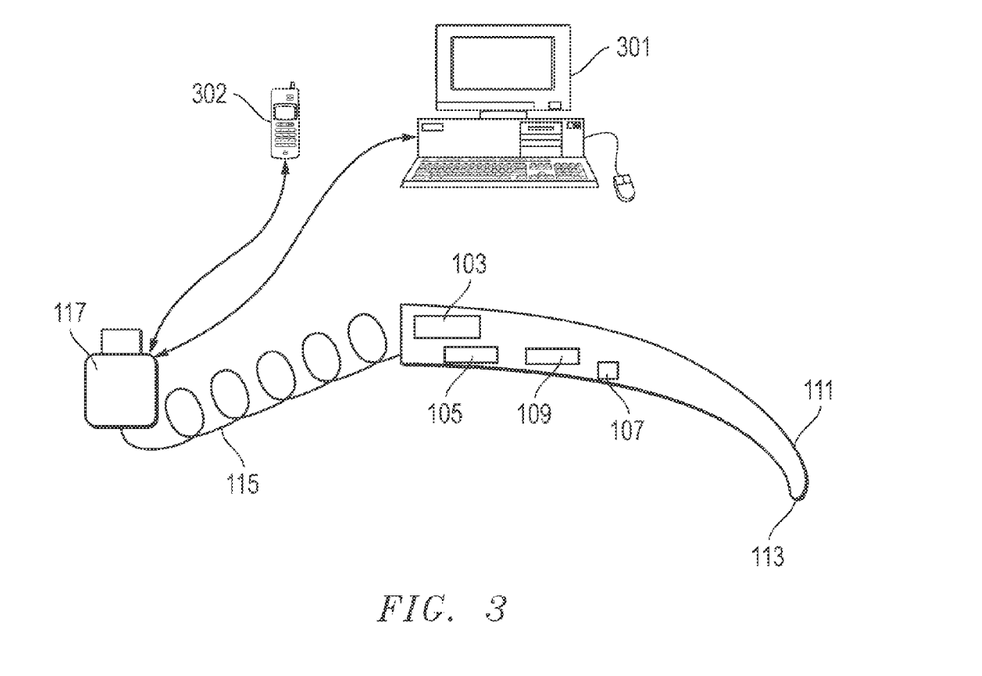
FIG. 3 is a schematic diagram of the intelligent preprogrammed thermometer connected by a USB cord to either a computer or a woman's personal electronic device.
Figure 4:
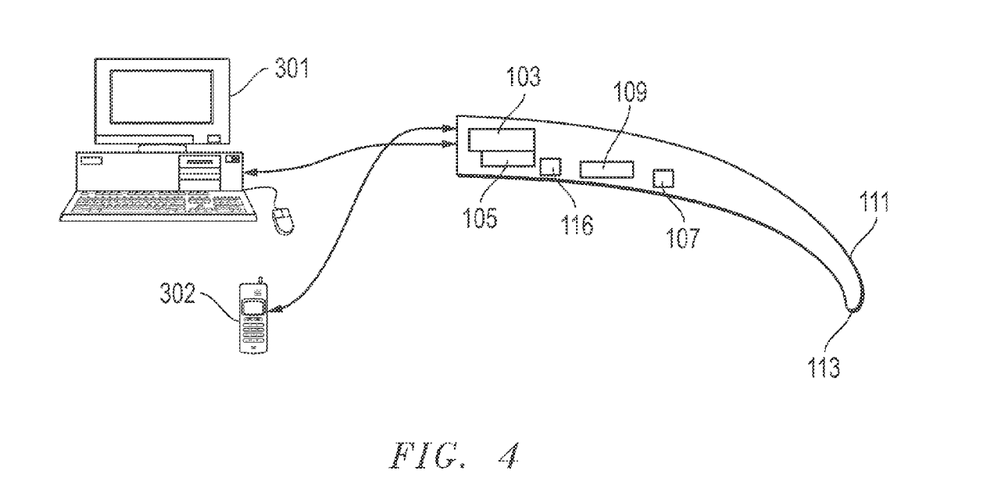
FIG. 4 is a schematic diagram of the intelligent preprogrammed thermometer connected wirelessly to either a computer or a woman's personal electronic device.

FIG. 3 and FIG. 4 each illustrate the computing devices necessary to operate the thermometer 101 with the application software 202. FIG. 3 illustrates the use of the thermometer 101 with the USB connector 117, connecting to either a personal computer. 301 or to a smart phone. 302. FIG. 4 illustrates the use of the thermometer 101 with the chip 116 to connect wirelessly to either a personal computer 301 (such as a tablet PC or a PC/Mac) or to a smart phone 302.

The application software 202 necessary for the operation of the thermometer 101 can be downloaded via an application software store or a website. The application software 202 works with either the personal computer 301 or the smart phone 302. The thermometer 101 communicates and exchanges information (individual cycle and BBT data) with the application software 202. The daily BBT measurements from the user are synchronized with the application software 202 in Degrees or Fahrenheit. Menstruation data, fertility status, cycle day, ovulation day and other detected cycle information are synchronized with the application software 202.

If the thermometer 101 connects via the USB 117 to a personal computer 301, then the power supply can be derived from the personal computer 301, and data transfer is possible at any time as long as there is a connection. On the other hand, if the thermometer 101 connects wirelessly via the chip 116, then data transfer will only be possible if the smart phone 302 is active. This feature allows for minimized power consumption during standby.

To extend battery life, in the preferred embodiment, the thermometer 101 goes into standby mode after sixty seconds with no user interaction or running a measurement. The recorded temperature and menstruation data, as well as the results of the cycle evaluation, are stored permanently and independently from the battery state.

For connection via the USB connector 117, a profile is used, which is commonly accepted (for example. HID, mass storage device or serial port interface). If the thermometer 101 is connected to a computer 301 that accepts the USB connector 117, then power can be drawn from the computer 301, and the thermometer 101 will act as "USB device". If the USB connector 117 is capable to act as a "USB device" only, the thermometer 101 has to act as a USB-on-the-go host.

The wireless (for example, Bluetooth) protocol may be implemented in a separate interface device inside the thermometer 101, or integrated into the microcontroller chip 103.

Figure 5:
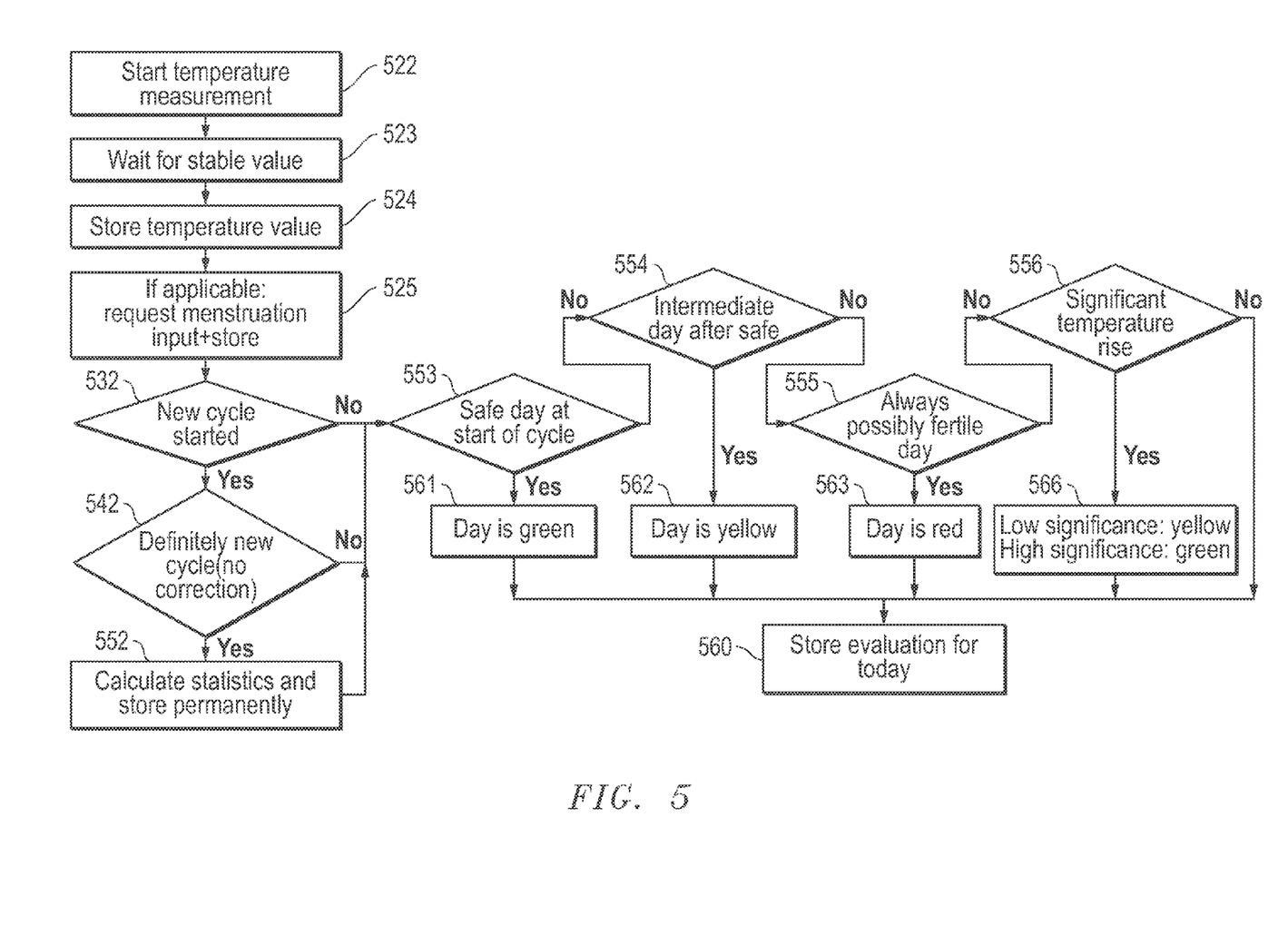
FIG. 5 is a flow chart of the method that the system of the present invention uses to record, store, and analyze the BBT, and to display the significance of the BBT.

Referring now to FIG. 5, the method is illustrated that the thermometer 101 uses to record, store, and analyze the BBT on the microcontroller chip 103. In step 522, the thermometer 101 starts measuring the temperature of the user. In step 523, the microcontroller chip 103 waits for a stable temperature value. In step 524, the user's cycle data (temperature) is saved and stored. The microcontroller chip 103 detects ovulation by the change of temperature and the input of the menstruation data. If applicable, in step 525, the chip 103 requests menstruation input, and stores that input. Based on the recorded data in steps 524 and 525, the chip 103 performs the following calculations. In step 532, the chip 103 determines the beginning of a new cycle, based on the menstruation day that the user previously entered in step 525, either using the application software 202, or on the thermometer 101. To achieve a definite detection of cycle start, dependent on the phase of the cycle, in step 542 the chip 103 determines whether three consecutive days of menstruation entry have occurred. If such has happened, then in step 552 the chip 103 calculates the statistics and stores them permanently.

Referring back to step 532, if a new cycle has hot started, or, if in step 542 the answer is also "no", then in step 553 the chip 103 processes the information and calculates accordingly to detect fertile levels. In step 553 the chip 103 determines whether the day is a "safe" day for avoiding conception, that is, at the start of a cycle. If it is, then in step 561 the chip 103 displays "infertile" (green signal). If in step 553 the chip determines that the day is NOT a "safe" day for avoiding conception, then in step 554 the chip 103 determines whether the day is an intermediate day after a "safe" day, that is, an "uncertain" day. If the chip 103 determines that the day is an "uncertain" day for avoiding conception, then in step 562 it displays "uncertain" or "possibly fertile" (yellow signal). If in step 554 the chip 103 determines that the day is NOT an "uncertain" day for avoiding conception, then in step 555 it determines whether the day is a possibly fertile day. If in step 555 the chip 103 determines that the day is a possibly fertile day, them in step 563 it displays "fertile" (red signal). If in step 555 the chip 103 determines that the day is NOT a possibly fertile day, then in step 556 it determines whether the measured temperature denotes a significant temperature rise. If the temperature rise is of low significance, then in step 566 it displays "possibly fertile" (yellow signal). If the temperature rise is of high significance, then in step 566 it displays "infertile" (green signal). If in step 556 the chip 103 determines that the temperature rise is not significant, then in step 560 the chip 103 stores and evaluates the result. In step 560, based on the day, of the cycle and the temperature readings, the chip 103 determines whether ovulation has already taken place in this cycle, and generates a display of fertility state. The chip 103 displays the result on the thermometer 101, and also makes the display available via the application software 202 on the personal computer 301 or on the smart phone 302. The actions in step 560 also occur after each of steps 561, 562, 563, and 566.

The chip 103 uses several measures to get a failsafe handling of temperature recordings. First, in step 523, temperature measurement is not finished until the value has, stabilized. If the temperature decreases significantly during the measurement, the value is not accepted until the temperature rises again to an acceptable value. This is because normally the basal body temperature will not significantly fall during the short period of measurement. Falling values thus are due to improper handling of the sensor 113, breathing cold air, or similar influences which impede getting valid data. Another measure used to get a failsafe handling of temperature recordings is that temperature values are evaluated with statistical methods, and require a high significance for an accepted temperature rise. A third measure used to get a failsafe handling of temperature recordings is that the required level, of significance is adapted over the cycle to integrate the probabilities of temperature and day of cycle.

The user has the possibility to correct her data (regarding menstruation and intercourse), using the application software 202 or the thermometer 101, backwards for a limited number of days (three days, in the preferred embodiment). As soon as a new cycle start is definitely detected in step 542 and can't be erased again, a complete evaluation of the finished cycle takes place (exact determination of ovulation day, average temperature values for pre- and post-ovulation, checking if a corpus luteum insufficiency, ("CLI") can be diagnosed or a monophase occurred) and the overall-statistics concerning the whole recorded data are updated.

Figure 6:
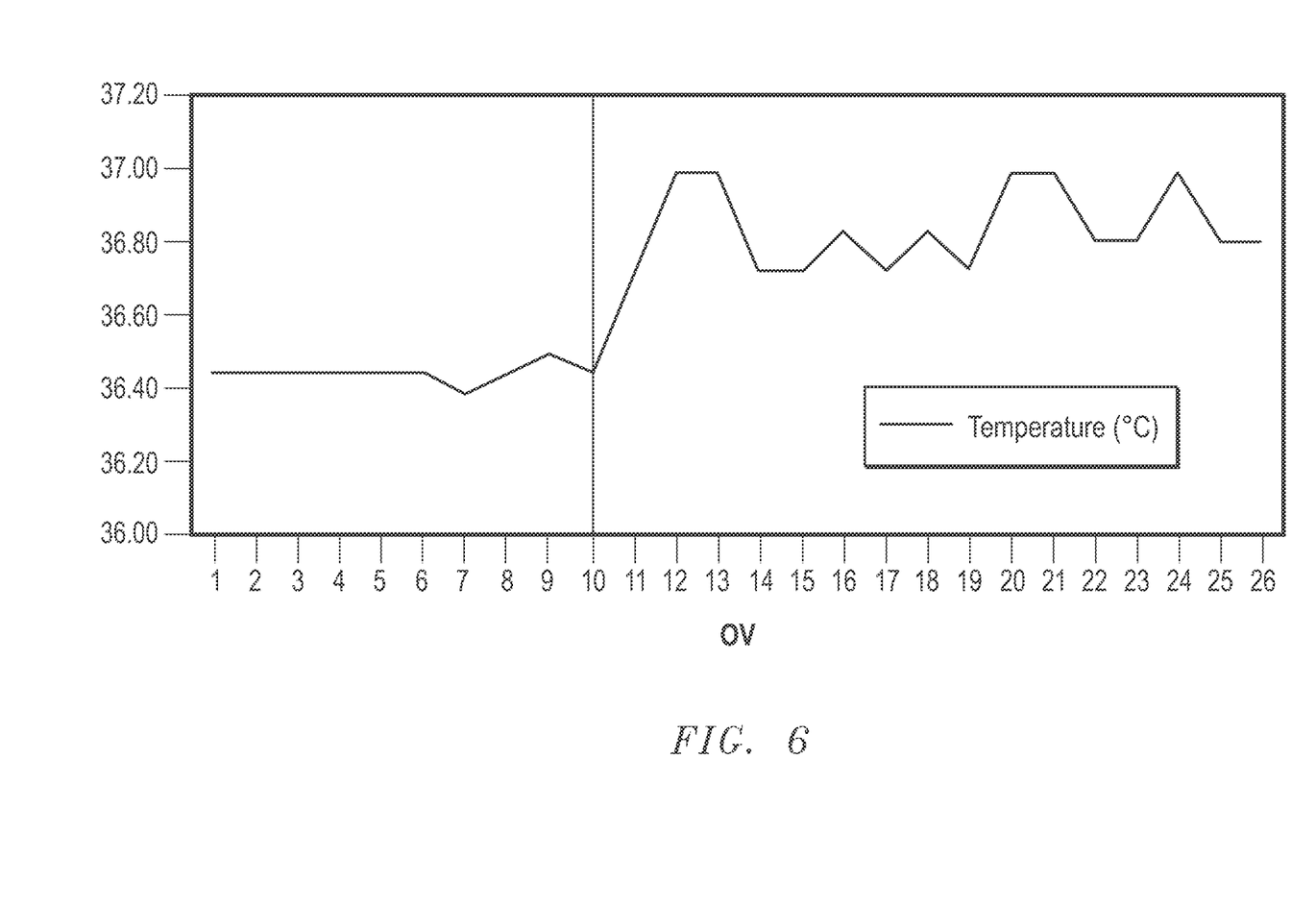
FIG. 6 is a graph illustrating the fluctuation of a woman's BBT during her monthly cycle.

FIG. 6. shows how the basal body temperature fluctuates in a woman's cycle. The menstrual cycle of a woman can be shorter (for example, 26 days) or longer (for example, 42 days) than the "average". Temperature rises during ovulation by just 0.25 to 0.45 degree Celsius. The thermometer 101 detects this slight temperature increase. Temperature falls when menstruation starts. Pre-ovulatory phase temperature is lower. Post-ovulatory phase temperature is higher.

Figure 7:
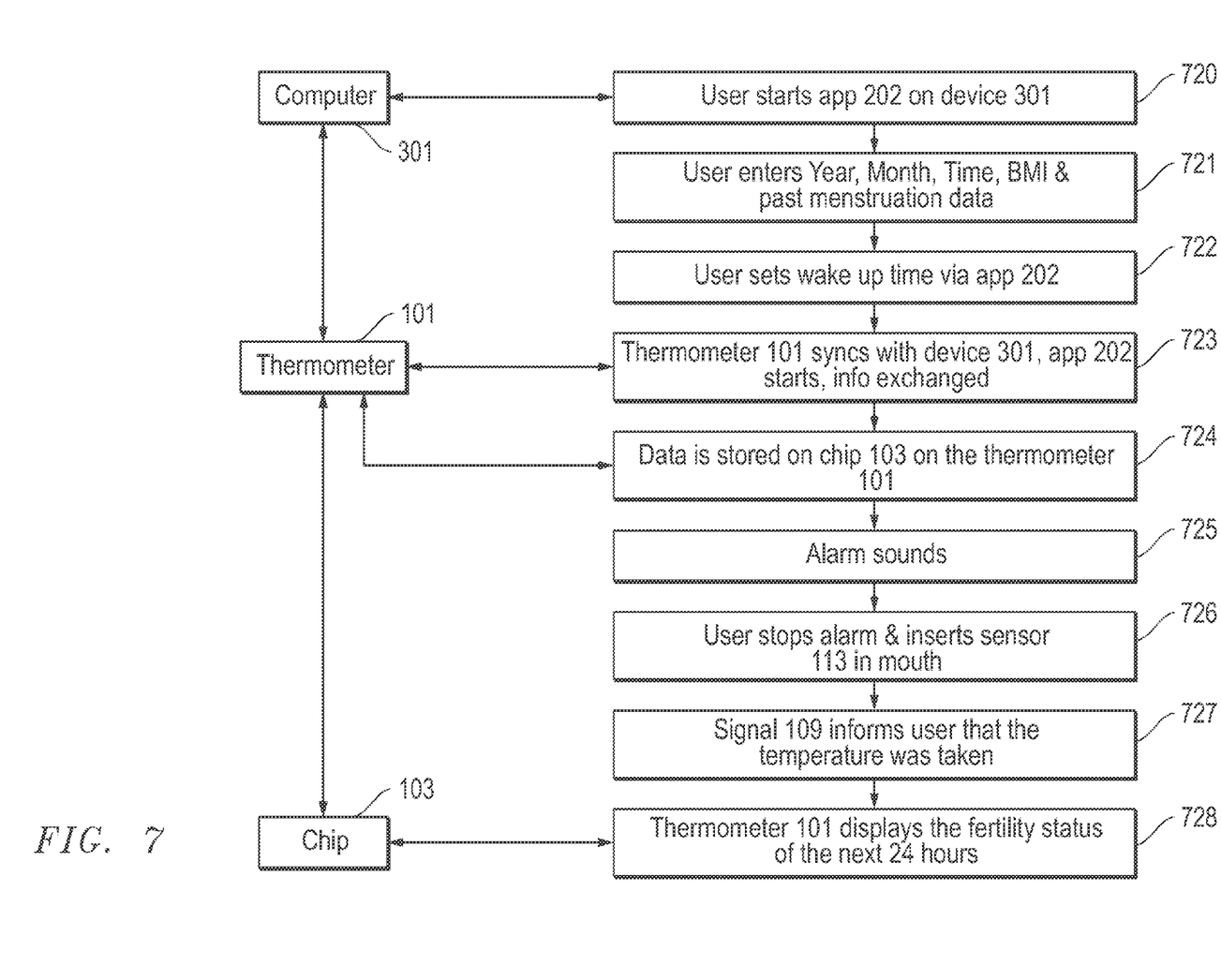
FIG. 7 is a flow chart of the usual method of the actions that the user of the system of the present invention would take, and the responses of the system to those actions.

Referring now to FIG. 7, the operation and use of the thermometer 103 is illustrated in a flowchart. The user of the thermometer 101 downloads the application software 202 from the inventor's website or an app store to a computer 301 or to a smart phone 302. In step 720, the application software 202 is opened and started. In step 721, the Year, Month, Day, Time, BMI and past menstruation data (if applicable) are entered and displayed via the application software 202, using the screens 231, 232, and 234. This is a one-time data entry. In step 722, the user sets the wake up time using, the application software 202 and the screen 242. In step 723, the thermometer 101 is synced with the computer 301, and information is exchanged. In step 724, data is stored on the chip 103. In step 725, the alarm on the thermometer 101 sounds at the time entered via, the application software 202. An optional feature allows the user to choose to be awakened by the smart phone 302, as can be set via the application software 202, using the screen 242. In step 726, the user stops the alarm by pressing the button 107 or by putting the end of the thermometer 101 containing the sensor 113 in her mouth. She then takes her temperature for about sixty seconds. In step 727, an acoustic or light signal 109 informs the user that her temperature was taken. In step 728, the chip 103 processes the data from the pre-entered data from the application software 202 and from the temperature just taken, and displays the fertility status of the next 24 hours. An optional feature allows the thermometer 101 to be synchronized with the application software 202 to display the fertility status and further cycle information, as shown in the display screens 243, 244, and 245. If menstruation occurs it can be so noted by the user, as shown in FIG. 5.

The application software 202 and the thermometer 101 can be synchronized anytime. Cycle data information of the user can be exchanged between the application software 202 and the thermometer 101 whenever wanted. Valuable information about the user's menstruation cycle can be viewed using the application software 202 through either a computer 301 or a smart phone 302.

What is claimed is:

1. A method of recording, storing, analyzing, and displaying changes in a woman's basal body temperature, comprising the steps of:
   (a) Connecting an intelligent, preprogrammed thermometer and an application software on a personal electronic device;
   (b) Exchanging personal data and basal body temperature data bi-directionally between the thermometer and electronic device for synchronizing the thermometer and the electronic device;
   (c) Determining inside the thermometer whether a current time is within a temperature reading time limit;
   (d) Recording with the intelligent, preprogrammed thermometer the woman's orally-measured temperature if the current time is within the temperature reading time limit;
   (e) Storing in the thermometer the woman's temperature to create a stored temperature reading;
   (f) Repeating steps (c), (d) and (e) to thereby create a plurality of stored temperature readings;
   (g) Analyzing inside the thermometer the significance of any changes in the stored temperature readings; and
   (h) Displaying the changes in the woman's basal body temperature, and displaying an analysis of those changes, on the thermometer, and on the electronic device connected to the thermometer.

2. The method according to claim 1, wherein steps (c), (d) and (e) are repeated daily when the woman first awakes from her night's sleep.

3. The method according to claim 2, wherein the woman first inputs into the thermometer data about herself, including at least her year of birth, her height, her weight, her body mass index, and her current and past menstruation data.

4. The method according to claim 3, wherein the thermometer plainly indicates whether the day is a "safe" day for avoiding conception.

5. The method according to claim 1, wherein (d) Recording includes measuring the length of time that the thermometer is inside the woman's mouth, determining the optimum length of time to measure her temperature, and activating an alarm to alert the woman when the optimum length of time has been reached.

6. A method comprising the steps of:
(a) Connecting an intelligent, preprogrammed thermometer and an application software on a personal electronic device;
(b) Entering additional data, including personal personal data and menstruation data of the woman, into the thermometer;
(c) Exchanging data bi-directionally between the thermometer and electronic device for synchronizing the thermometer and the electronic device;
(d) Recording with an intelligent, preprogrammed thermometer a women's orally-measured temperature;
(e) Storing in the thermometer the woman's temperature to create a stored temperature reading;
(f) Repeating (d) and (e) to thereby create a plurality of stored temperature readings;
(g) Analysing inside the thermometer the significance of any changes in the stored temperature readings; and
(h) Displaying a fertility status based on an analysis of those changes on the thermometer and on the electronic device,
wherein, in step b), the additional data can be entered both directly on the thermometer and indirectly via direct entry on the electronic device.

7. The method of claim 6 wherein menstruation days entered by the woman are used to calculate the fertility status.

8. The method of claim 6, further comprising displaying menstruation status on the thermometer and on the electronic device.

9. The method of claim 6, wherein the fertility status is displayed with red and green LEDs on the thermometer.

10. The method of claim 6, wherein the electronic device is a mobile phone.

11. The method of claim 6, wherein the electronic device is a smart phone.

12. The method of claim 6, wherein the electronic device is a tablet computer.

13. The method of claim 6, wherein the electronic device displays the fertility status for the woman's past cycle and further displays a prediction of the fertility status for the woman's next cycle.

14. The method of claim 6,
wherein the additional data entered can be corrected on both the electronic device and the thermometer.

15. The method of claim 6, wherein the communicating between the thermometer and electronic device is performed using a wireless protocol.

16. The method of claim 15, wherein the wireless protocol is Bluetooth.

17. The method of claim 6, further comprising communicating between the thermometer and the electronic device using a cable coupled therebetween.

18. The method of claim 17, wherein the communicating is performed using USB.

19. The method of claim 15, wherein wireless communication is limited to the transfer of temperature data.

* * * * *